United States Patent [19]
Kajiyama

[11] Patent Number: 5,814,504
[45] Date of Patent: Sep. 29, 1998

[54] PROTEIN INVOLVED IN REGENERATING FIREFLY LUCIFERIN

[75] Inventor: Naoki Kajiyama, Chiba, Japan

[73] Assignee: Kikkoman Corporation, Noda, Japan

[21] Appl. No.: 869,996

[22] Filed: Jun. 5, 1997

Related U.S. Application Data

[60] Provisional application No. 60/024,671 Aug. 22, 1996.
[51] Int. Cl.$^6$ .............................. C12N 9/62; C12Q 1/66; A63J 1/00
[52] U.S. Cl. ............................. 435/189; 435/8; 530/417
[58] Field of Search ............................. 435/8, 218, 189; 530/350, 412, 415, 417

[56] References Cited

PUBLICATIONS

Strehler, "Bioluminescence assay. Principles and practice", Method Biochem. Anal. (1968) 16: 99–181.

"New Riverside University Dictionary"(Riverside Publishing Co., Boston) (1994) p. 480 and 680.

Johnson et al. "Bacterial and other 'luciferins'", Bioscience (1975) 25(11): 718–722, Nov. 1975.

Okada et al. "Firefly Bioluminescence III. Conversion of oxyluciferin to luciferin in firefly", Tetrahedron Lett. (1974) 32: 2771–2774.

McCapra et al. "Biosynthesis of luciferin in Pyrophorus pellucens", J. Chem. Soc. Comm. (1976) 5: 153–154, Mar. 1976.

*Primary Examiner*—Jon P. Weber
*Assistant Examiner*—Susan Hanley
*Attorney, Agent, or Firm*—Oblon, Spivak, McClelland, Maier & Neustadt, P.C.

[57] ABSTRACT

A purified protein having a molecular weight of 40 kD by SDS-PAGE that produces firefly luciferin when combined with D-cysteine and firefly oxyluciferin and isolated from firefly species is provided, as well as methods of making and using the protein for the continuous regeneration of of firefly luciferin.

20 Claims, No Drawings

PROTEIN INVOLVED IN REGENERATING FIREFLY LUCIFERIN

PROTEIN INVOLVED IN REGENERATING FIREFLY LUCIFERIN

This application is a continuation of Provisional application No. 60/024,671, filed Aug. 22,1996.

FIELD OF THE INVENTION

The present invention relates to a protein involved in regenerating luciferin.

BACKGROUND OF THE INVENTION

Bioluminescence is a luciferase reaction of catalyzing oxidation of luciferin as a luminescence substrate, and oxyluciferin is formed as the reaction product.

This oxyluciferin is known as an inhibitor of this luciferase reaction, so the luminescence of the luciferin/luciferase reaction is known to be rapidly decreased after flash luminescence immediately after the reaction.

Under the existing circumstances, no protein acting on oxyluciferin to regenerate luciferin as the luminescence substrate has been isolated and purified.

If such protein is found and added to the luciferin/luciferase reaction system, improvements in durability of luminescence can be expected and will lead to e.g. reduction of the amount of luciferase and luciferin used.

SUMMARY OF THE INVENTION

The object of the present invention is to provide a protein having the ability to regenerate luciferin by acting on oxyluciferin and D-cysteine.

As a result of their eager research, the present inventors found that a protein having the ability to regenerate luciferin by acting on oxyluciferin and D-cysteine is present in living Coleoptera, and they successfully isolated and purified the protein.

That is, the present invention provides the following inventions:

(1) A protein having the ability to regenerate luciferin by acting on oxyluciferin and D-cysteine.

(2) A protein having the ability to regenerate luciferin by acting on oxyluciferin and D-cysteine, which is obtained by purifying an extract from a living body capable of luminescence through purification steps including a chromatographic step.

(3) The protein according to (2), wherein the living body capable of luminescence is a Coleoptera.

(4) The protein according to (2), wherein the living body capable of luminescence is a firefly.

(5) The protein according to (2), wherein the living body capable of luminescence is a North American firefly.

(6) The protein according to (2), wherein the living body capable of luminescence is a Japanese firefly.

(7) The protein according to (2), wherein the living body capable of luminescence is *Luciola cruciata*.

(8) The protein according to (2), wherein the living body capable of luminescence is *Luciola lateralis*.

DETAILED DESCRIPTION OF THE INVENTION

Hereinafter, the present invention is described in detail.

To produce the present protein, any method may be used. For example, mention may be made of the following method.

The source of the present protein is not limited insofar as it contains the present protein. Examples of such sources include Coleoptera such as fireflies, commercially available crude enzyme extracts from fireflies, and recombinants produced by use of genetic recombination means.

Then, such sources containing the present protein are disrupted, lyzed or solubilized in a buffer.

The buffer is not limited unless the present protein is inactivated in it. Examples are Tris buffer, phosphate buffer, glycylglycine buffer etc.

For destruction, a mortar and mortar rod, a homogenizer, a Warning blender, a French press etc. may be used. For lyzing, treatment with lysozyme etc. may be used.

Then, a crude enzyme solution is obtained by centrifuging or filtering the disrupted, lyzed or solubilized materials in a usual manner to remove residues. If necessary, crude enzyme powder may be obtained from the crude enzyme solution by suitable adoption of ammonium sulfate precipitation, alcohol precipitation, acetone precipitation etc.

A purified enzyme preparation can be obtained from the crude enzyme solution or crude enzyme powder by a suitable adoption of the following techniques: gel filtration using Sephadex, Ultrogel, Bio-Gel etc., an adsorption-elution method using ion exchangers, electrophoresis using polyacrylamide gel etc., an adsorption-elution method using hydroxyapatite, sedimentation such as sucrose density gradient centrifugation etc., separation based on a difference in isoelectric point, affinity chromatography, fractionation using molecular sieve membrane, hollow fiber membrane etc.

The effect of the present invention is as follows: a protein having the ability to regenerate luciferin by acting on oxyluciferin and D-cysteine is provided according to the present invention, and by adding this protein to a luciferin/luciferase reaction system the luminescence can persist and the amount of luciferase and luciferin used can be reduced.

EXAMPLES

Hereinafter, the present invention is described in more detail by reference to Examples.

Example 1

4 g firefly lantern extract (SIGMA) was dissolved in 200 ml buffer A (pH 7.0), i.e. 25 mM tris(hydroxymethyl) aminomethane-hydrochloric acid (Tris-HCl) buffer containing 100 mM sodium chloride, 1 mM dithiothreitol, 1 mM disodium ethylenediaminetetraacetate, and 10 % (W/V) glycerol.

The solution thus obtained was precipitated with ammonium sulfate in a usual manner, and the precipitates occurring between 40 to 60 % saturation with ammonium sulfate were dissolved in 20 ml buffer A.

Then, this solution was subjected to gel filtration chromatography by passing it through a column of Ultrogel AcA34 (IBF) previously equilibrated with buffer A to give an active fraction.

The fraction thus obtained was dialyzed against buffer B (pH 6.5), i.e. 5 mM TRIS-HCl buffer containing 1 mM dithiothreitol, 1 mM disodium ethylenediaminetetraacetate, 5 % (W/V) glycerol, and 1 mm sodium chloride.

The resulting solution was adsorbed onto a column of S-Sepharose FF (Pharmacia Biotech) previously equilibrated with buffer B, and the protein was eluted in a linear gradient of 1–100 mm NaCl to give an active fraction.

The active fraction thus obtained was dialyzed against buffer C (a solution at pH 8.0 with the same composition as buffer B), then adsorbed onto an ion-exchange HPLC column (TSK gel Super Q-5PW, available from Tosoh Corporation) previously equilibrated with buffer C, and the protein was eluted in a linear gradient of 1–100 mM NaCl to give an active fraction.

The active fraction thus obtained could be successfully purified by passing it through a gel filtration HPLC column (TSK gel G3000SWXL, available from Tosoh Corporation) previously equilibrated with buffer A.

The fraction after this gel filtration was analyzed by SDS-PAGE (Laemmli, U.K.: Nature, 227, 680, (1970)). The result indicated that the molecular weight of the purified protein was about 40,000.

The optimum pH and optimum temperature of the present protein were pH 7–8 and 35–50 °C. respectively. The present protein maintained 80 % or more of the original activity even after thermal treatment at 50 °C. for 30 minutes.

Example 2

Luminous organs from 200 fireflies (*Luciola cruciata*) (purchased from Seibu Department Store) were added to 15 ml buffer A, then disrupted with Hiscotoron (NITI-ON Medical and Physical Instrument Manufacturing), and centrifuged at 12,000 r.p.m. for 20 minutes to give 14 ml supernatant as a crude enzyme.

This crude enzyme solution was precipitated with ammonium sulfate, and the precipitates occurring between 30 and 60 % saturation with sulfate ammonium were separated by centrifugation at 12,000 r.p.m. for 10 minutes and then dissolved in 20 ml buffer A.

This solution was subjected to gel filtration through Ultrogel AcA34 (IBF) previously equilibrated with buffer A to give an active fraction.

The solution thus obtained was dialyzed against buffer B (pH 6.5) and then adsorbed onto a column of S-Sepharose FF (Pharmacia Biotech) previously equilibrated with buffer B, and the protein was eluted in a linear gradient of 1–100 mM NaCl to give an active fraction.

The active fraction thus obtained was dialyzed against buffer C (a solution at pH 8.0 with the same composition as buffer B), then adsorbed onto an ion-exchange HPLC column (TSK gel Super Q-5PW, available from Tosoh Corporation) previously equilibrated with buffer C, and the protein was eluted in a linear gradient of 1–100 mM NaCl to give an active fraction.

The active fraction thus obtained could be successfully purified by passing it through a gel filtration HPLC column (TSK gel G3000SWXL, available from Tosoh Corporation) previously equilibrated with buffer A. The optimum pH and optimum temperature of the present protein were pH 7–8 and 35–50 °C. respectively. The present protein maintained 80 % or more of the original activity even after thermal treatment at 50 °C. for 30 minutes.

Example 3

Luminous organs from 300 fireflies (*Luciola lateralis*) (purchased from Seibu Department Store) were added to 15 ml buffer A, then disrupted with Hiscotoron ™(NITI-ON Medical and Physical Instrument Manufacturing), and centrifuged at 12,000 r.p.m. for 20 minutes to give 13 ml supernatant as a crude enzyme.

This crude enzyme solution could be successfully purified in the same procedures as in Example 2.

The optimum pH and optimum temperature of the present protein were pH 8–9 and 50–70 °C. respectively. The present protein maintained 80 % or more activity even after thermal treatment at 50 °C. for 30 minutes, or 60 % or more activity even after thermal treatment at 60 °C. for 30 minutes.

Example 4

The effect on the luciferin/luciferase reaction of the protein purified in Example 1 was examined. 10 μl of the protein purified in Example 1 was added to a mixture of 10 μl of 0.5 μg/ml American firefly luciferase, 40 μl of 1 mM luciferin, 40 μl of 10 mM D-cysteine, and 300 μl of an activity measurement buffer (25 mM glycylglycine plus 5.4 mM magnesium sulfate (pH 7.8)). 100 μl of 10 mM ATP was introduced into this solution, and the intensity of the luminescence occurring was measured at 10-second intervals for 1 minute. The results are shown in the table below. As the control, 10 μl of the activity measurement buffer was used in place of the protein. As a result, it was found that the addition of the present protein improves the durability of luminescence.

TABLE

| Time (seconds) | 10 | 20 | 30 | 40 | 50 | 60 |
| --- | --- | --- | --- | --- | --- | --- |
| Protein added (Kcount) | 7.9 | 6.5 | 6.5 | 6.5 | 6.0 | 6.0 |
| Control (Kcount) | 5.1 | 3.7 | 3.2 | 3.0 | 3.0 | 2.8 |

The same effect could be confirmed as well when the protein purified in Example 2 and 3 was used. Measurement Activity Method A substrate mixture was prepared by adding 1 ml of 0.01 mM D-cysteine and 0.5 ml of 1 mM oxyluciferin to 8.5 ml of the activity measurement buffer (25 mM glycylglycine plus 5.4 mM magnesium sulfate (pH 7.8)).

10 μl of a measurement sample was added to 100 μl of the above mixture and reacted at 37 °C. for 4 hours. This reaction solution, 10 μl was added to 200 μl of the activity measurement buffer, followed by introduction of 100 μl ATP/luciferase mixture (i.e. 0.5 mg/ml luciferase in 10 mM ATP), and the luminescence occurring for 5 seconds was accumulated.

What is claimed is:

1. An isolated and purified protein obtained from a firefly species which converts firefly oxyluciferin and D-cysteine to firefly luciferin.

2. The protein of claim 1, which has a molecular weight of about 40,000 Daltons as measured by SDS-PAGE, an optimum pH of 7 to 8, and an optimum temperature of 35 to 50° C.

3. The protein of claim 2, which is isolated from firefly lantern extract.

4. The protein of claim 1, which has an optimum pH of 7 to 8 and an optimum temperature of 35 to 50° C.

5. The protein of claim 1, which has an optimum pH of 8 to 9 and an optimum temperature of 50 to 70° C.

6. The protein of claim 1, wherein said firefly species is a North American firefly.

7. The protein of claim 1, wherein said firefly species is a Japanese firefly.

8. The protein of claim 1, wherein said firefly species is *Luciola cruciata*.

9. The protein of claim 1, wherein said firefly species is *Luciola lateralis*.

10. The protein of claim 1, which is obtained by a process comprising isolating said protein from an extract of a firefly species which produces said prote in.

11. A method of producing the protein of claim 1, comprising isolating said protein from an extract of a firefly species which produces said protein.

12. The method of claim 11, comprising:

(a) providing a firefly extract;

(b) contacting the extract of step (a) with ammonium sulfate to produce a precipitate, and collecting said precipitate between 30 to 60% saturation of ammonium sulfate ;

(c) subjecting the collected precipitate of step (b) to gel filtration chromatography to obtain a first eluate;

(d) subjecting the first eluate of step (c) to ion exchange chromatography to obtain a second eluate;

(e) subjecting the second eluate of step (d) to gel filtration chromatography to obtain a third eluate;

(f) isolating said purified protein from the third eluate.

13. The method of claim 12, wherein the first eluate is subjected to cation exchange chromatography in step (c).

14. A method of producing the protein of claim 2, comprising isolating said protein from an extract of a firefly species which produces said protein.

15. A method of producing the protein of claim 3, comprising isolating said protein from an extract of a firefly species which produces said protein.

16. A method of producing the protein of claim 4, comprising isolating said protein from an extract of a firefly species which produces said protein.

17. A method of producing firefly luciferin, comprising contacting firefly oxyluciferin and D-cysteine with the protein of claim 1, thereby producing said firefly luciferin.

18. A method of producing firefly luciferin, comprising contacting firefly oxyluciferin and D-cysteine with the protein of claim 2, thereby producing said firefly luciferin.

19. A method of producing firefly luciferin, comprising contacting firefly oxyluciferin and D-cysteine with the protein of claim 3 thereby producing said firefly luciferin.

20. A method of producing firefly luciferin, comprising contacting firefly oxyluciferin and D-cysteine with the protein of claim 4, thereby producing said firefly luciferin.

* * * * *